United States Patent [19]

Hirsch

[11] Patent Number: 5,582,620
[45] Date of Patent: Dec. 10, 1996

[54] RADIAL DISTENTION OF A SOFT TISSUE SPACE USING A FINGER GUIDED DISTENTION BALLOON

[75] Inventor: Irvin H. Hirsch, Bala Cynwyd, Pa.

[73] Assignee: Thomas Jefferson University, Philadelphia, Pa.

[21] Appl. No.: 527,955

[22] Filed: Sep. 14, 1995

[51] Int. Cl.[6] ............................ A61B 17/00; A41D 19/00
[52] U.S. Cl. .................. 606/192; 600/207; 2/161.7
[58] Field of Search .................................. 606/191, 192, 606/194, 195, 198, 119; 604/96–101; 2/159, 161.8, 161.7, 160, 162, 168, 221; 600/207

[56] References Cited

U.S. PATENT DOCUMENTS

| | | |
|---|---|---|
| 1,170,324 | 2/1916 | Pomerene . |
| 2,394,140 | 2/1946 | Biscow . |
| 3,672,351 | 6/1972 | Ubersax et al. . |
| 3,992,723 | 11/1976 | Lazanas ..................... 2/161.7 |
| 4,013,077 | 3/1977 | Ritota et al. . |
| 4,245,656 | 1/1981 | Farr et al. . |
| 4,473,079 | 9/1984 | Jasper et al. . |
| 4,920,974 | 5/1990 | Roth et al. . |
| 5,071,429 | 12/1991 | Pinchuk et al. . |
| 5,309,896 | 5/1994 | Moll et al. . |
| 5,383,889 | 1/1995 | Warner et al. . |
| 5,526,536 | 6/1996 | Cartmill ..................... 2/162 |

FOREIGN PATENT DOCUMENTS 11910 of 1897 United Kingdom .

OTHER PUBLICATIONS

Gaur, D. D., "Laparoscopic Operative Retroperitoneoscopy: Use of a New Device", *The J. of Urology* 1992, 148, 1137–1139.
Hirsch, I. H. et al., "Facilitated Implantation of the Inguinal Reservoir of the Multicomponent Inflatable Penile Prosthesis", *The J. of Urology* 1994, 152, 142–143.
Preperitoneal Distention Balloon™ System Product Brochure, Origin Medsystems, Inc., Menlo Park, CA, 1992.

Primary Examiner—Michael Powell Buiz
Assistant Examiner—William Lewis
Attorney, Agent, or Firm—Woodcock Washburn Kurtz Mackiewicz & Norris

[57] ABSTRACT

A device for radially distending a soft tissue space comprising a finger sheath for covering at least one finger. The sheath has a proximal and distal end. A distention balloon is attached to the distal end of the sheath. The balloon has a relative deflatable position in relation to the finger sheath and a relative inflatable position in relation to the sheath. An inflation source for inflating the distention balloon to a preferred volume thereby dilating the desired the soft tissue space is provided. A valve member for deflating the balloon is also provided.

47 Claims, 8 Drawing Sheets

RADIAL DISTENTION OF A SOFT TISSUE SPACE USING A FINGER GUIDED DISTENTION BALLOON

FIELD OF THE INVENTION

This invention relates to medical devices and the methods for using the medical device. More particularly the invention relates to the methods and medical devices that are used to radially distend a soft tissue space within a patient's body.

BACKGROUND OF THE INVENTION

Many surgical techniques require the dilation of a hollow bodily area within a patient's body to perform an ensuing medical procedure. Surgeons and veterinarians may use a rigid trocar or catheter like instrument having a distention balloon affixed thereto to dilate that bodily area. There are many prior art medical devices that are used in this capacity.

Such medical procedures that may require the use of a distention balloon include hernia operations, penile implant operations, breast augmentation and implant operations, operations to insert a cardiac pacemaker, operations to apply a neurostimulator implant, laparoscopic surgery, and almost any other operation that requires a hollow working cavity or blunt dissection of tissues.

The procedure to dilate a hollow bodily area in a patient's body includes an incision through the patient's skin, a blunt sweeping dissection of the skin tissue with either a surgical instrument or a surgeon's finger, and a "blind distention" of the desired area. This medical procedure, therefore, necessitates the application of a large dose of an anesthetic to the patient. When using the anesthetic, however, it is not always possible to determine the exact dosage to administer to a patient. Also the anesthesia, will not prevent trauma to the patient.

Different degrees of trauma can be caused by maneuvering the rigid medical device within the body. By moving the rigid medical instrument around in a patient's body, there is a strong likelihood that the patient will sustain intraoperative hemorrhaging, post-operation hematoma, and post-operation morbidity.

After the operation, the rigid medical instrument must be sterilized. The sterilization of the medical instrument requires a sterilizing chemical which may add costs to the medical fees.

An example of a medical procedure that incorporates the use of a rigid trocar having a distention balloon affixed thereto is the medical procedure to implant a multi-component inflatable penal prosthesis as described in the article from The Journal of Urology, Vol. 152, pp 142–143, July 1994, titled "Facilitated Implantation of the Inguinal Reservoir of the Multi-Component Inflatable Penile Prosthesis" by Irvin H. Hirsch, Jose Moreno and Leonard G. Gomella. This article is incorporated by reference into this description.

The prior art medical procedure for the implantation of a inguinal reservoir of the multi-component inflatable penile prosthesis as described in the article, permits a one-step creation of an adequate prevesical space. The preperitoneal distention balloon is inflated in the prevesical space to produce a compartment of adequate volume to avoid back pressure on the reservoir and minimize potential bladder injury in the setting of previous pelvic surgery.

Various techniques are used to facilitate implantation of the inguinal reservoir of the multi-component inflatable prosthesis by a penoscrotal approach. One technique requires creating a separate open inguinal incision to access the prevesical space, and blindly sweeping the prevesical fascia and fat to accommodate the reservoir. Alternatively, an inguinal reservoir inserter has been designed to facilitate insertion of the reservoir by a single penoscrotal incision. The former technique requires a separate incision and closure.

Placement of the inguinal reservoir potentially may cause bladder or blood vessel injury. Also, both of the described techniques require an uncontrolled blunt dissection to create an adequate compartment for the 100 ml reservoir.

Recent advances in facilitating extraperitoneal laparoscopic approaches by balloon dilation have been developed that may be extended to this part of the implant operation. The preperitoneal distention balloon is routinely applied to facilitate implantation of the inguinal reservoir. The implications of this technique include shortened operative time, controlled one step distention of the prevesical goal space, assurance of adequate volume for the reservoir compartment and avoidance of injury to the structure surrounding the perivesical space. Based on this favorable experience, many surgical procedures may benefit by adding finger guidance and tactile control to the radial balloon distention.

SUMMARY OF THE INVENTION

It is an objective of the inventor to provide a medical instrument for facilitating soft tissue dilation that may shorten operation time, and minimize tissue trauma.

Another objective of the inventor is to provide a medical instrument for facilitating soft tissue dilation which provides a safer approach for identifying a desired plane of dissection.

Yet another objective is to provide a medical instrument for facilitating soft tissue dilation for an ensuing operation that minimizes inter-operation hemorrhage, postoperative hematoma and post-operation morbidity.

Still another objective is to provide a medical instrument and procedure for facilitating soft tissue dilation that may require the use of less anesthesia during an operation.

Yet another object of the invention is to provide a flexible disposable medical instrument for facilitating soft tissue dilation.

Additional objectives of the inventor and advantages of the invention will be set forth in part in the description which follows, and in part will be obvious from the description, or may be learned by practice on the invention. The objectives of the inventor and advantages of the invention may be realized and attained by means of the instrumentalities and combinations particularly pointed out in the appended claims.

To achieve the objectives and in accordance with the purpose of the invention as embodied and broadly described herein, one embodiment of a medical instrument for radially distending a soft tissue body space comprises a flexible material that covers at least one finger of a hand. This flexible material has a distal end and a proximal end. An inflatable balloon is attached to the distal end of the flexible material. The balloon has a relative deflatable position and a relative inflatable position in relation to the flexible material. When the flexible material is inserted into a hollow portion in a body and the balloon is in the inflatable position, the hollow area in the body will dilate.

Another embodiment of the device for radially distending a soft tissue space comprises a flexible glove. The glove has at least one finger compartment for receiving a finger. The finger compartment has a proximal end and a distal end. A distention balloon is attached to the distal end. The distention balloon has a relative deflatable and relative inflatable position in relation to the glove. When the device is placed within the hollow portion of a body and the balloon is inflated to its desired volume, the hollow body portion will dilate thereby allowing an ensuing medical procedure to take place.

In another embodiment of the present invention, the device for radially distending a soft tissue space comprises a finger sheath for covering at least one finger of a hand. The sheath has a proximal end and a distal end. A distention balloon is attached to the distal end of at least one finger. The balloon has a relative deflatable position and a relative inflatable position in relation to the finger sheath. When the finger sheath is inserted into a hollow portion of a body and the balloon is inflated to its desired volume, the hollow body portion will dilate thereby allowing an ensuing medical procedure to take place.

In another embodiment of the present invention, the device for the radially distention of a soft tissue space comprises a mitten for covering a hand. The mitten has a compartment for receiving fingers of a hand. The mitten has a proximal end and a distal end. A distention balloon is attached to the mitten distal end. The balloon has a relative inflatable and a relative deflatable position in relation to the mitten. When the mitten is inserted into a hollow portion of a body and the balloon is in inflated to its desired volume, the soft tissue space dilates thereby allowing an ensuing medical procedure to take place.

Another aspect of the present invention is the method of manipulating a patient's internal body area so that an ensuing medical procedure can take place. The method comprises the steps of creating an incision through a patient's skin. The next step is the insertion of at least one finger that is covered with a surgical protective material that has a distention balloon coupled thereto, into the patient's interior bodily area that will be dilated. The distention balloon is then inflated to its preferred volume so that the desired interior bodily area will dilate allowing an ensuing medical procedure to be completed.

BRIEF DESCRIPTION OF THE DRAWINGS

The accompanying drawings which are incorporated in and constitute a part of the specification, illustrate one embodiment of the invention and together with the description, serve to explain the principles of the invention.

The invention will now be further described by way of example, with reference to the accompanying drawings, in which.

DETAILED DESCRIPTION OF THE INVENTION

Reference will now be made in detail to the present preferred embodiment of the invention, an example of which is illustrated in the accompanying drawings. It is noted that like materials or parts are designated by the same numeral throughout the drawings.

Figure 1:
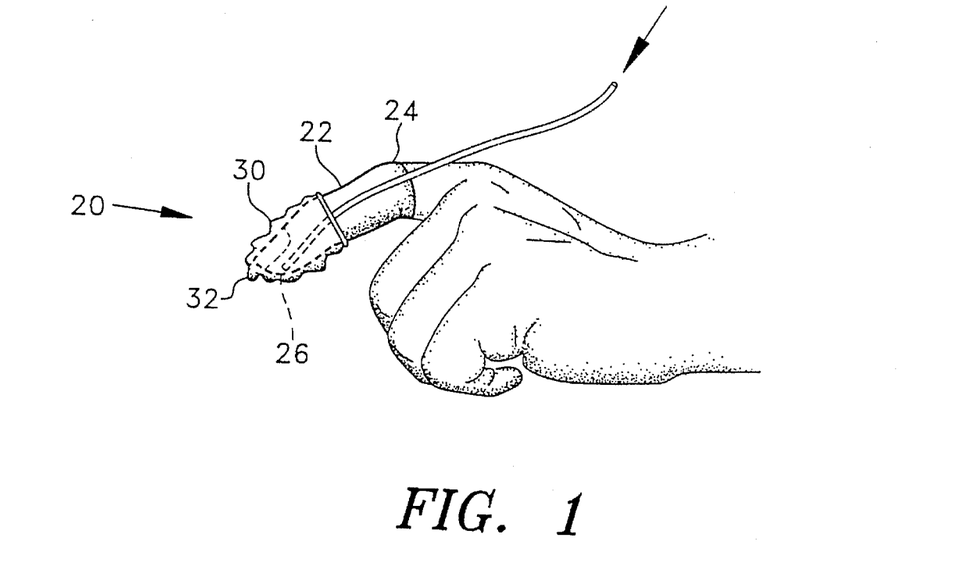
FIG. 1 is a perspective view of one embodiment in accordance with the present invention in a deflated position.
Figure 2:
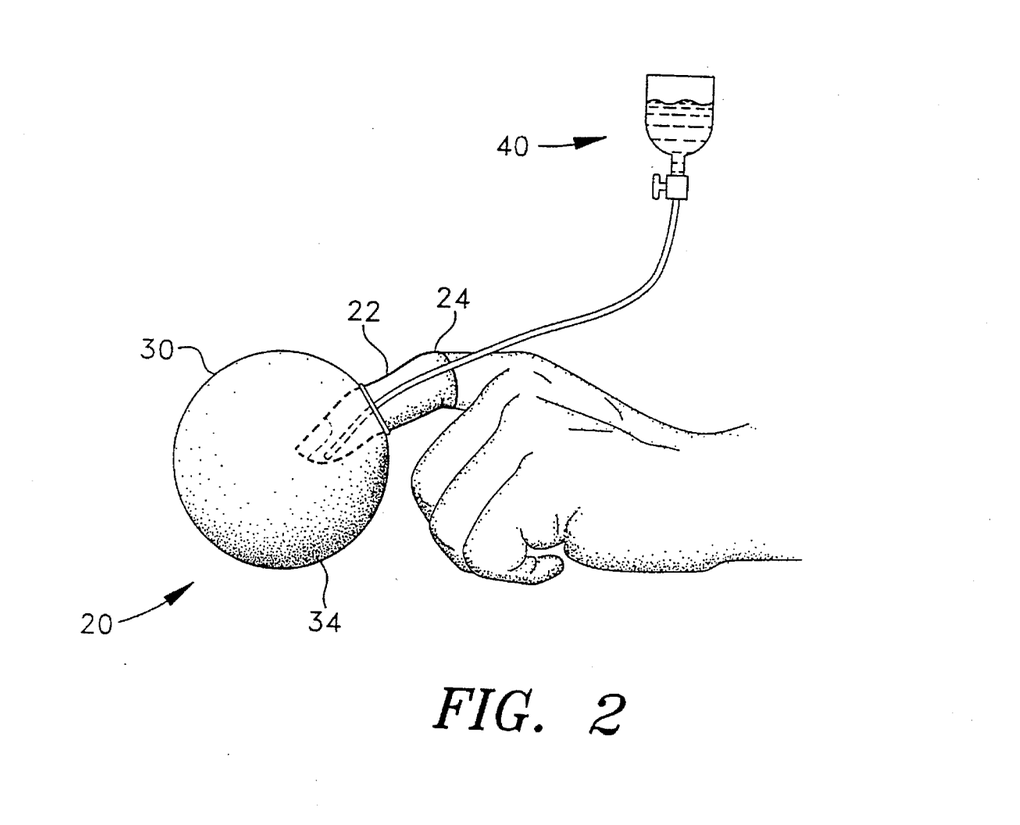
FIG. 2 is a perspective view of the preferred embodiment in an inflated position.
Figure 3:
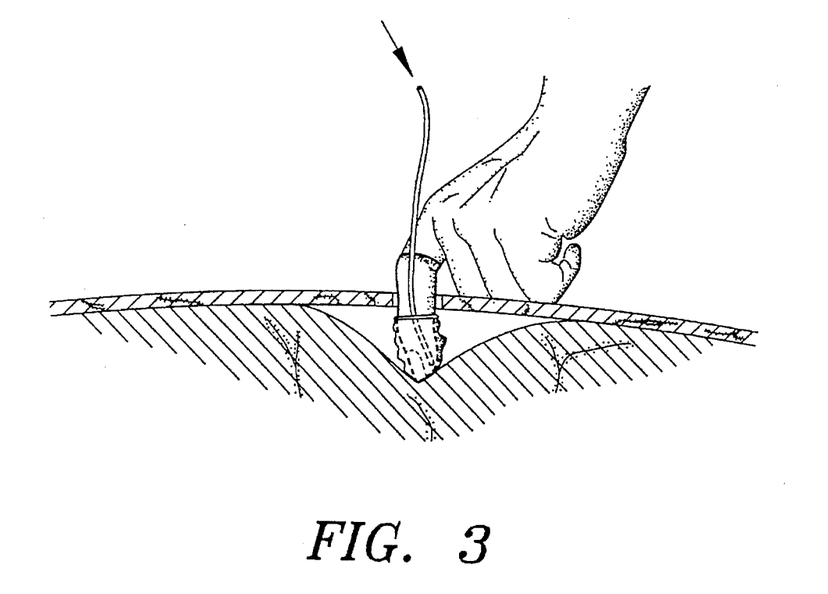
FIG. 3 is a perspective view of the preferred embodiment in one step of a medical operation.

The preferred embodiment of the medical instrument for radially distending a soft tissue body space is shown in FIGS. 1 and 2 and is represented generally by the numeral 20. The medical instrument comprises a flexible finger sheath 22. The finger sheath be made formed to at least fit over a doctor's palparing index finger made from any one of several commercially available materials such as a silicone material or other flexible surgical material. The finger sheath can be manufactured by following the methods used by those skilled in the art who routinely make surgical gloves and other like products.

The finger sheath 22 has a proximal end 24 and a distal end 26. A distention balloon 30 is attached to the distal end 26. The distention balloon can be attached to the finger sheath with adhesives, clips, bonding methods, and the like. The balloon is attached by standard balloon/catheter angioplasty technology used by those skilled in the art.

There are a variety of distention balloons that are commercially available. The particular shape and size of the distention balloon that is used will depend on the particular operation that is required (spherical, pancake, longitudinal, oblong or ovoid). For example, a spherical preperitoneal distention balloon, which is made by Origin Medsystems, located in Menlo Park, Calif., ranges in dilation volumes of 50 to 1000 ml and is used for penile implant operations. By contrast a pancake or ovid distention balloon, which is used during a proposed procedure, may range in distention volumes of 50 to 1500 ml.

The distention balloon has a relative deflatable position 32 and a relative inflatable position 34 in relation to the finger sheath 22. A fluid flow assembly for inflating and deflating the distention balloon is shown in FIG. 2 and is designated by the numeral 40. The fluid flow assembly is coupled to the distention balloon. The fluid flow conduit may lie either on the inside or outside of the finger sheath, but will preferably be on the outside so as not to interfere with a surgeon's sense of touch.

The fluid flow assembly for inflating and deflating comprises at least one fluid flow control valve, at least one fluid chamber for storing a fluid for inflating the distention balloon, an inflating fluid, and at least one flow conduit for allowing the inflating fluid to flow into or out from the distention balloon.

The fluid conduit is coupled to both the distention balloon and to the fluid chamber that stores the fluid that will inflate the distention balloon. Such fluids include saline and air. The fluid flow control valves are coupled to the fluid conduit and fluid chamber to control the rate of fluid that flows through the fluid conduit and into or out of the distention balloon. Alternatively, a standard syringe can be used to inflate or deflate the balloon. The operation of "inflating" or "deflating" the distention balloon is routinely performed by those skilled in the art.

Figure 4A:
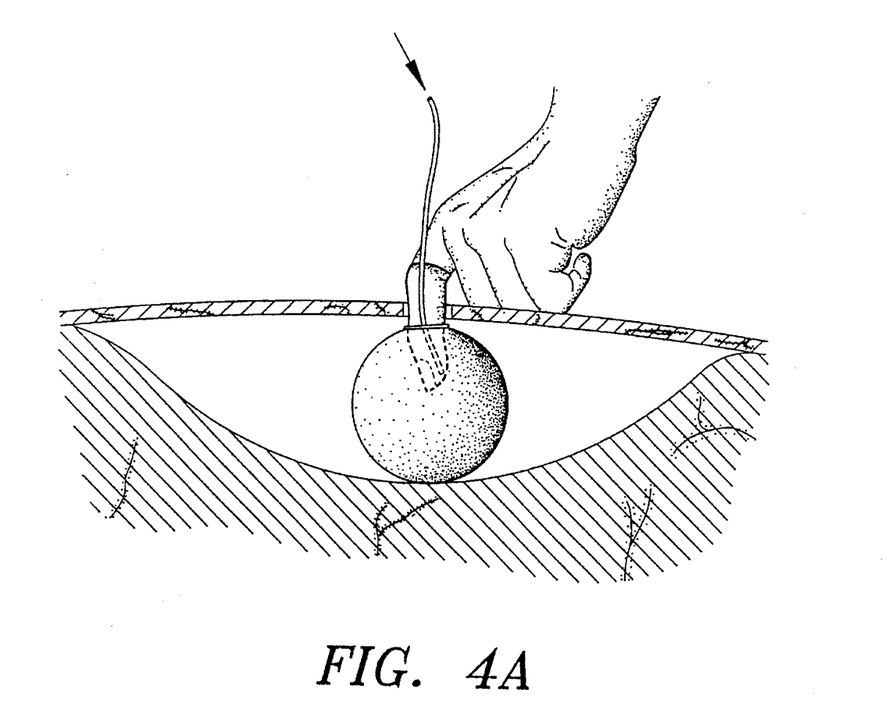
FIG. 4a is another perspective view of the preferred embodiment in another step of a medical procedure.
Figure 4B:
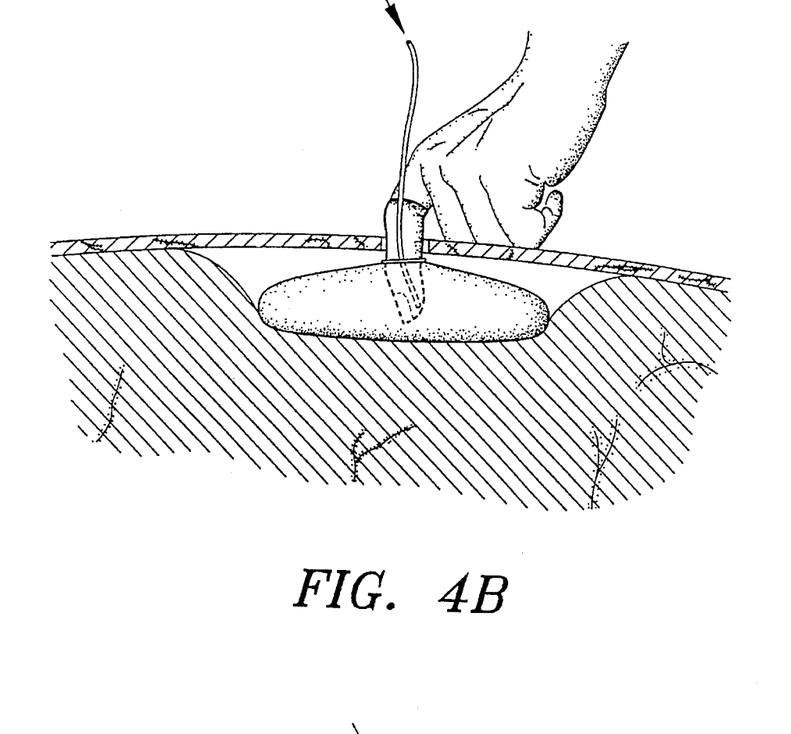
FIG. 4b is another perspective view of the preferred embodiment in the same step shown in FIG. 4 incorporating a pancake shaped balloon embodiment.
Figure 4C:
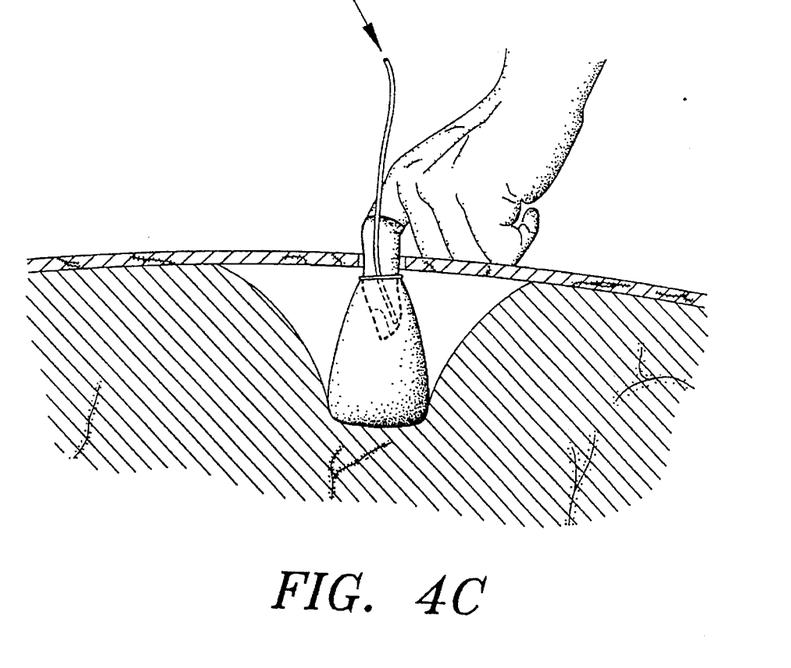
FIG. 4c is another perspective view of the preferred embodiment in the same step as shown in FIG. 4 incorporating an ovoid shape balloon embodiment.

FIGS. 4(a), 4(b), and 4(c) show various distention balloons in the relative inflated state. FIG. 4(b) depicts the present invention employing a pancake shaped balloon. The ovoid shaped balloon may be used for operations requiring organ mobilization. FIG. 4(c) depicts the present invention employing a ovid shaped balloon. The pancake shaped balloon may be used for operations requiring dissection of tissue planes.

Figure 5:
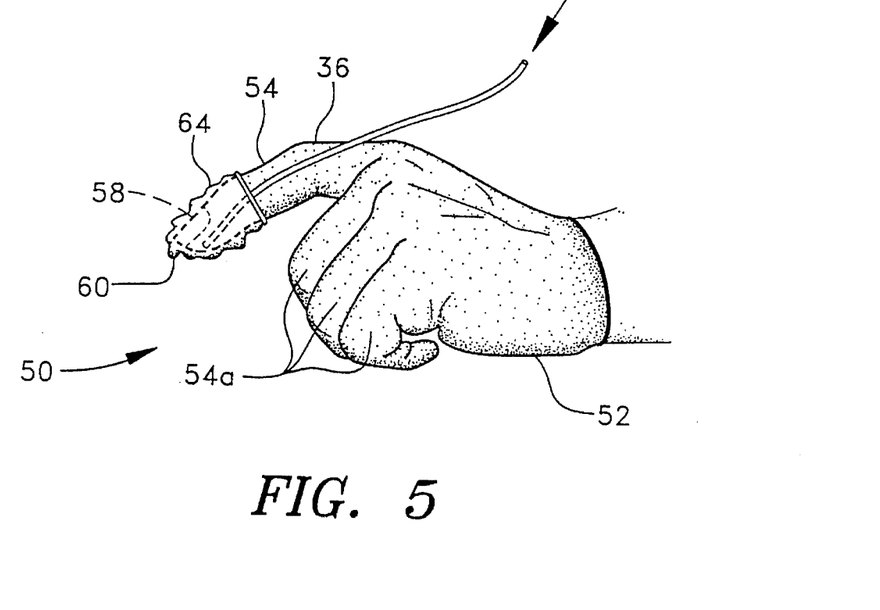
FIG. 5 is a perspective view of another embodiment of the present invention in a deflated position.
Figure 6:
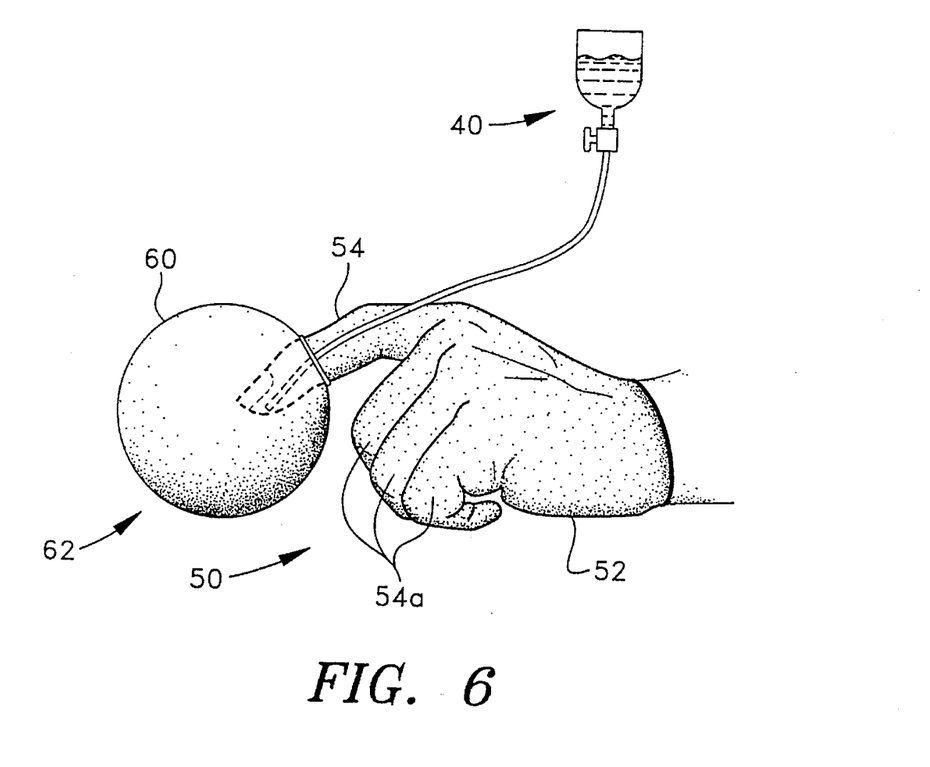
FIG. 6 is a perspective view of another embodiment of the present invention in an inflated position.
Figure 7:
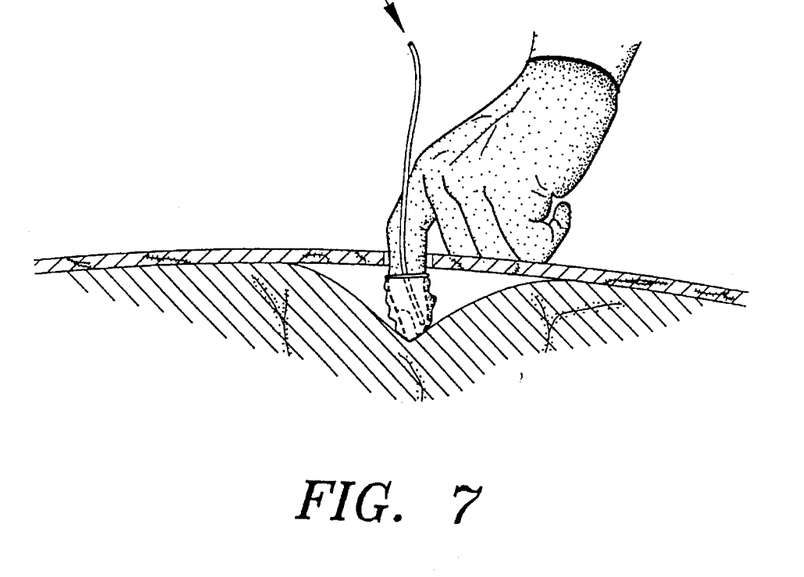
FIG. 7 is a perspective view of another embodiment of the present invention in one step of a medical operation.

Another embodiment of the present invention is shown in FIG. 5 and is generally designated by the numeral 50. This embodiment comprises a surgical glove 52 that is made from any one of several commercially available materials such as a silicone material or other flexible surgical material. The glove has at least one finger compartment 54 for covering at least one palparing finger of a hand although FIGS. 5 and 6 show that all of the fingers 54 a the hand are covered. The glove can be manufactured by following the methods used by those skilled in the art who routinely make surgical gloves and other like products.

The finger compartment has a proximal end 56 and distal end 58. A distention balloon 60 is attached to at least one finger compartment by an adhesive, clip, bonding methods and the like. Again, the particular shape and size of the distention balloon that is used will depend on the particular operation that is required. The distention balloon has a relative inflatable position 62 and a relative deflatable position 64 in relation to the glove. As shown in FIG. 6, a fluid flow assembly 40 for inflating and deflating the distention balloon is also coupled to the distention balloon.

The fluid flow assembly comprises at least one fluid flow control valve, at least one fluid chamber, an inflating fluid stored within the fluid chamber, and at least one flow conduit for allowing the saline to flow into or out from the distention balloon. The fluid conduit is coupled to both the distention balloon and the fluid chamber that stores the inflating fluid. The fluid flow control valves are coupled to the fluid conduit and fluid chamber to control the rate of fluid that flows into and out of the distention balloon. The fluid flow conduit may lie either on the inside or outside of the finger sheath, but is preferably located on the outside so as not to interfere with a surgeon's sense of touch. The operation of "inflating" and "deflating" the distention balloon are routinely performed by those skilled in the art.

Figure 8:
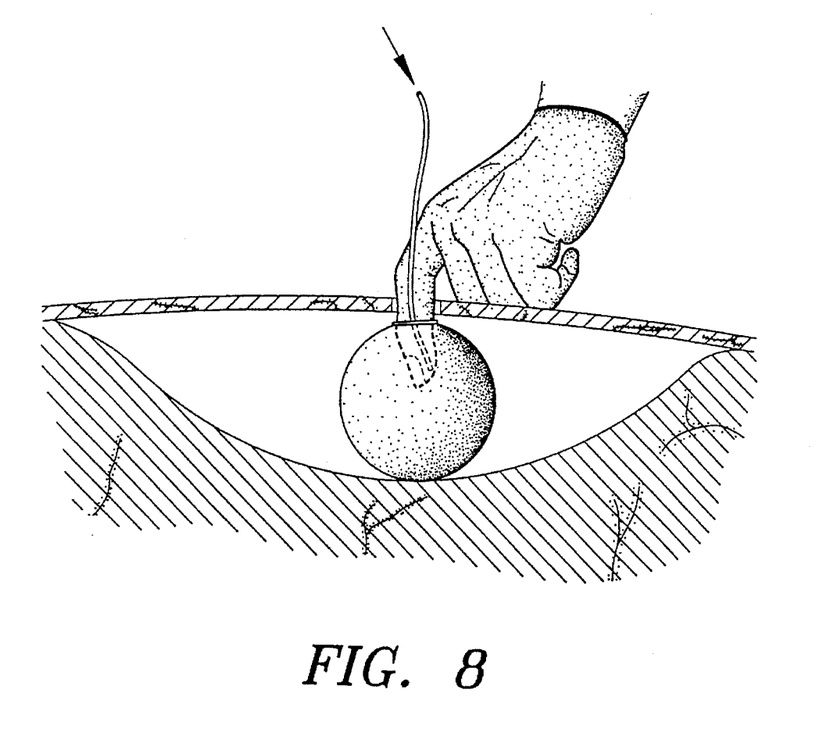
FIG. 8 is a perspective view of another embodiment of the present invention in another step of a medical operation.
Figure 8A:
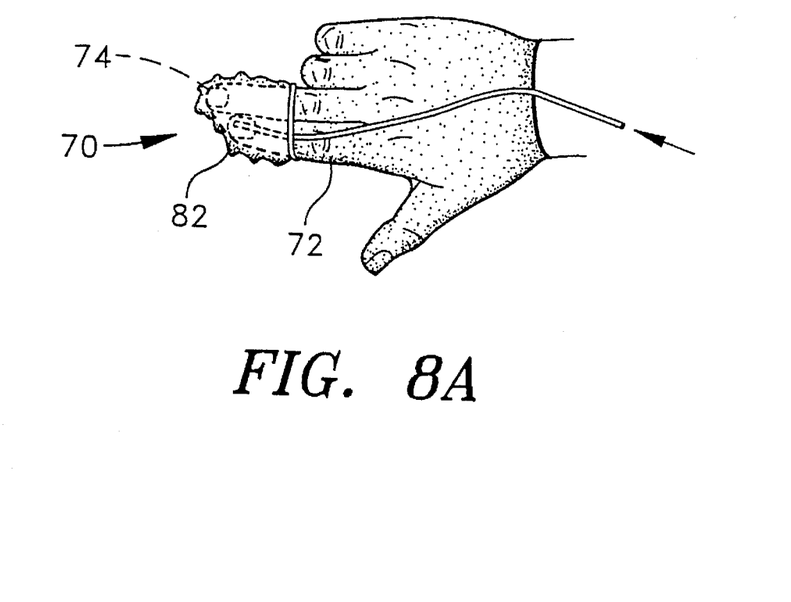
FIG. 8a is a perspective view of another embodiment of the present invention in a deflated position.
Figure 8B:
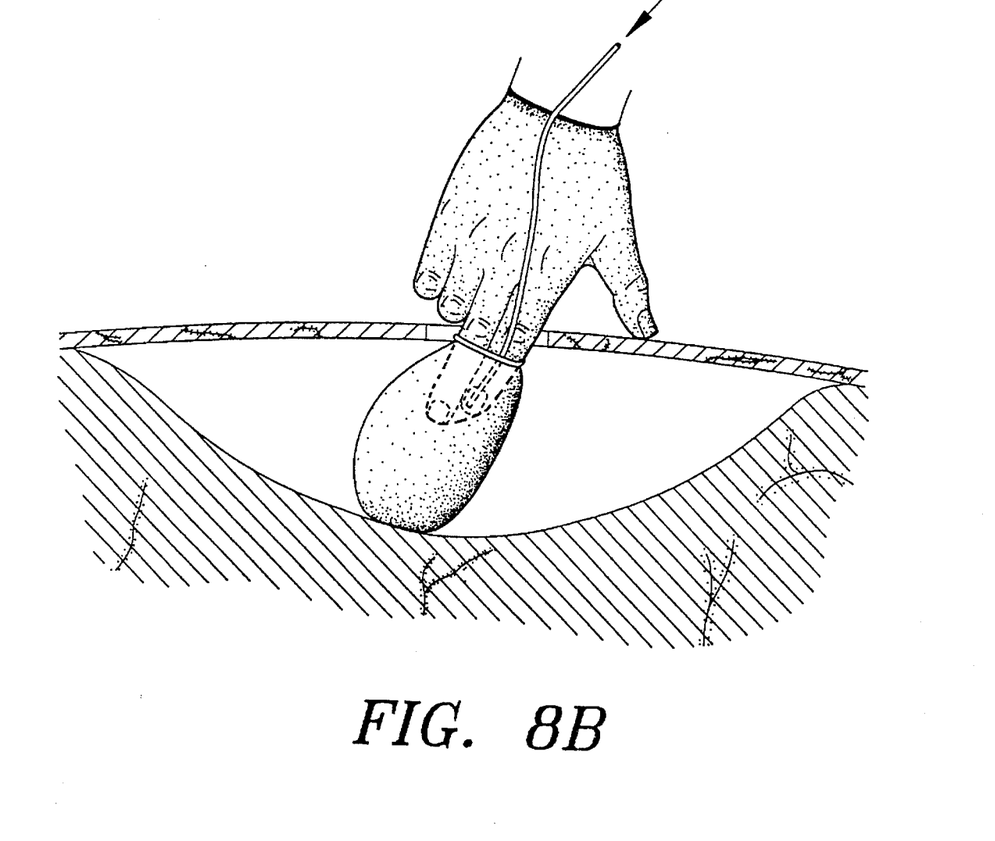
FIG. 8b is a perspective view of another embodiment of the present invention in one step of a medical operation.

An alternative embodiment of the present invention shown in FIG. 8(a) is generally designated as numeral 70. This device for radially distending a soft tissue space in a patient's body comprises a flexible surgical sheath that is capable of fitting over a doctor's index and middle fingers.

The sheath may be made from any one of several commercially available materials such as a silicone material or other flexible surgical material. The two-finger sheath can be manufactured by following the methods used by those skilled in the art who routinely make surgical gloves and other like products.

The two-finger sheath has a finger compartment 72 for receiving two fingers of a hand. The sheath has a proximal end 76 and a distal end 78. A distention balloon is attached to the distal end 80 with an adhesive, a clip, a bonding method or the like. The distention balloon has a relative inflatable position 82 any a relative deflatable position 84 in relation to the two-finger sheath. The particular size and shape of the distention balloon that is used will depend on the particular operation that is required. A fluid flow assembly 40 for inflating and deflating the distention balloon is also coupled to the distention balloon.

The fluid flow assembly comprises at least one fluid flow control valve, at least one fluid chamber, an inflating fluid stored within the fluid chamber, and at least one flow conduit for allowing the saline to flow into or out from the distention balloon. The fluid conduit is coupled to both the distention balloon and the fluid chamber that stores the inflating fluid. The fluid flow control valves are coupled to the fluid conduit and fluid chamber to control the rate of fluid that flows into and out of the distention balloon. The fluid flow conduit may lie either on the inside or outside of the finger sheath, but will preferably be located on the outside so as not to interfere with a surgeon's sense of touch. The operation of "inflating" and "deflating" the distention balloon are routinely performed by those skilled in the art.

The two finger sheath may be particularly useful for creating long, narrow spaces but may be used in other situations. The two-finger embodiment of the present invention may be used for prevesical space creation for implanting cylindrically shaped reservoirs, commercially available from the Mentor Corp. located in California. The two-finger embodiment may also be employed for general tissue dissection and organ mobilization (e.g. kidney and spleen).

Figure 9:
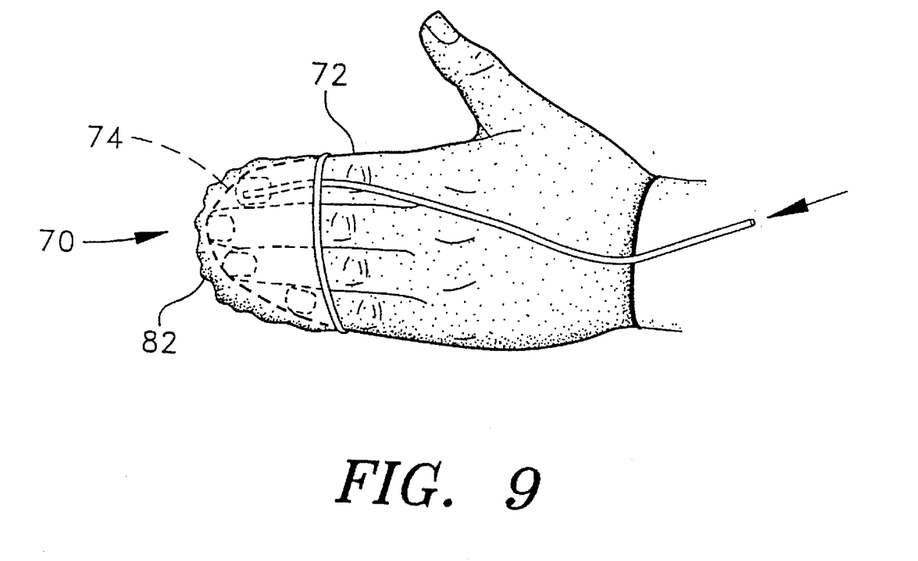
FIG. 9 is a perspective view of another embodiment of the present invention in a deflated position.
Figure 10:
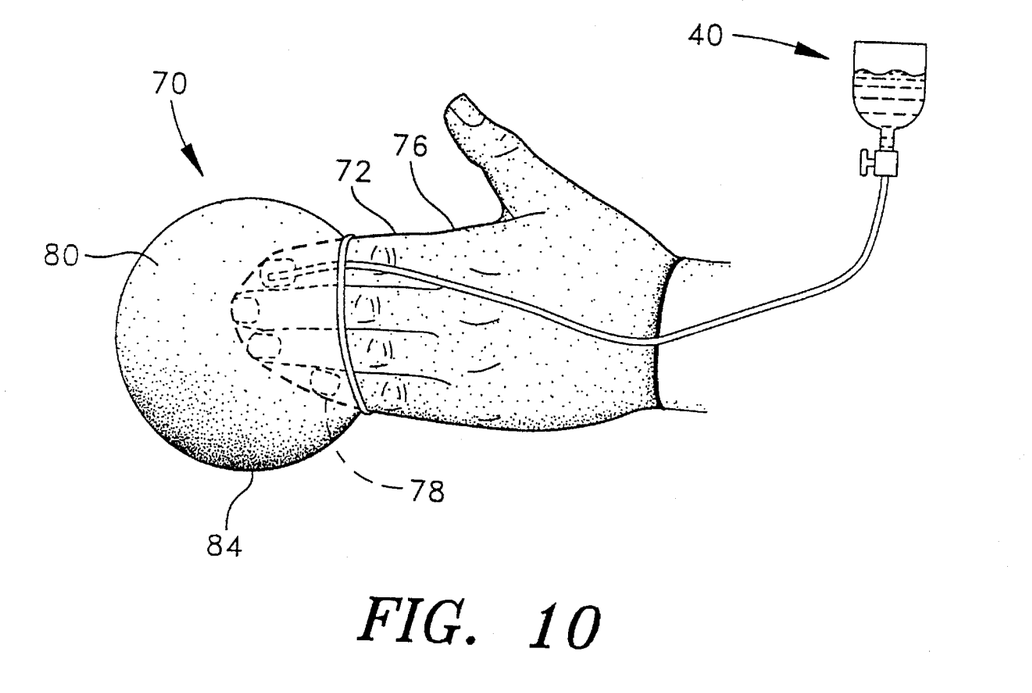
FIG. 10 is a perspective view of another embodiment of the present invention in a inflated position.
Figure 11:
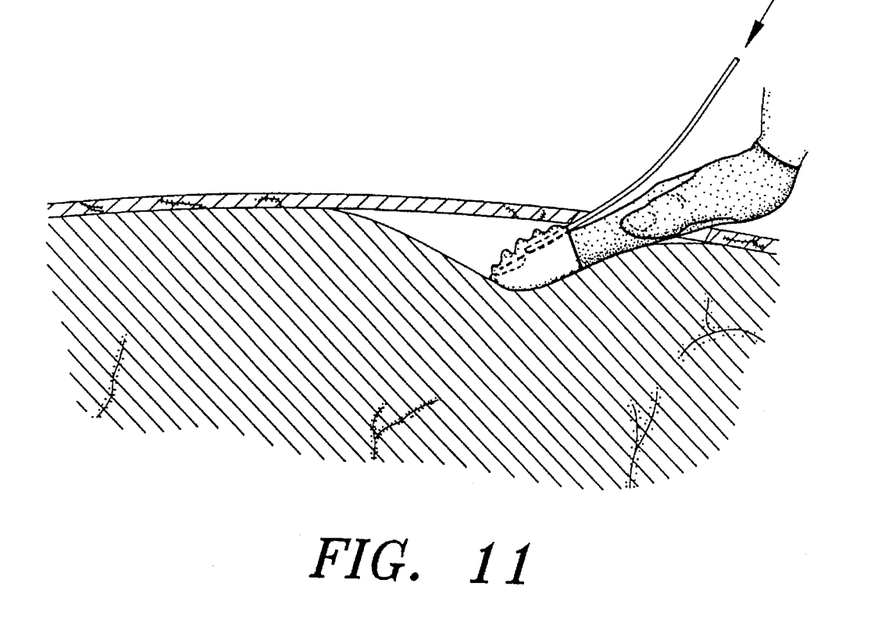
FIG. 11 is a perspective view of another embodiment of the present invention in one step of a medical operation.
Figure 12:
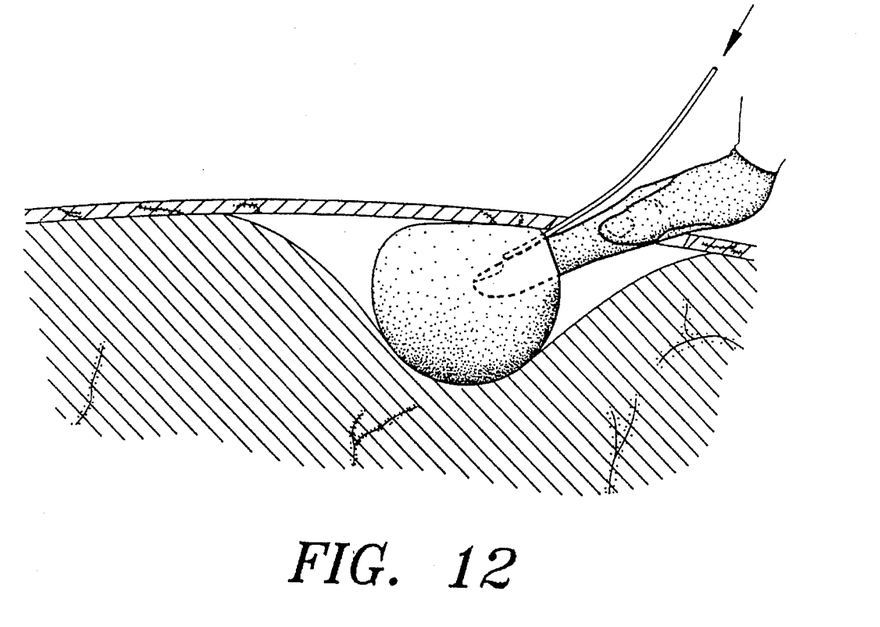
FIG. 12 is a perspective view of another embodiment of the present invention in another step of a medical operation.

A further embodiment of the present invention as shown in FIGS. 9 and 10 is generally designated as numeral 70. This device for radially distending a soft tissue space in a patient's body comprises a flexible surgical mitten 72 for covering a hand. The surgical mitten is made from any one of several commercially available materials such as a silicone material or other flexible surgical material.

The mitten 72 has a finger compartment 74 for receiving at least one finger of a hand. The mitten 72 has a proximal end 76 and a distal end 78. A distention balloon is attached to the distal end 80 with an adhesive, a clip, a bonding method or the like. The distention balloon has a relative inflatable position 82 and a relative deflatable position 84 in relation to the mitten 72. The particular shape and size of the distention balloon that is used will depend on the particular operation that is required. A fluid flow assembly 40 for inflating and deflating the distention balloon is also coupled to the distention balloon.

The fluid flow assembly 40 comprises at least one fluid flow control valve, at least one fluid chamber, an inflating fluid, and at least one flow conduit for allowing the saline to flow into or out from the distention balloon.

The flow conduit is coupled to both the distention balloon and the fluid chamber. The fluid conduit allows the inflating fluid to flow into the distention balloon thereby inflating the distention balloon. The fluid conduit also allows the inflating fluid to flow out from the distention balloon and travel back to the fluid chamber so that the distention balloon can return to the deflatable position. The operation of "inflating" and "deflating" the distention balloon are routinely performed by those skilled in the art.

The preferred method for manipulating a patients internal bodily area to allow an ensuing medical procedure to take place is shown in FIGS. 3, 4, 7, 8, 11 and 12 will know be described. The method comprises a doctor creating an incision through a patient's skin to permit access to the body interior to perform a medical procedure. After the incision the doctor will insert at least his/her palparing index finger which is covered with a flexible surgical protective material, such as a flexible silicone finger sheath, glove, or mitten; and has an inflatable and deflatable distention balloon coupled thereto into the patient's interior bodily area that will be dilated. The distention balloon is then inflated to the desired volume (see FIGS. 4, 8, and 12) by a fluid flow assembly.

After the distention balloon is inflated it will remain within the interior bodily area for a sufficient amount of time such that the interior bodily area can dilate wide enough so that an ensuing medical procedure can be completed. One example of the this method is during the implantation of a multi-component inflatable penile prosthesis. This medical procedure will now be described.

In this procedure, a penile implant, such as the AMS 700 cx or Ultrex plus model made by the American Medical Systems, Minnetonka, Minn., is implanted in a patient. The designated cylinder size requires the incorporation of a 100 cc inguinal reservoir. Following the closure of the corporotomies and dartos pouch containing the inflate/deflate device blunt and sharp dissection over the pubic ramus medial aspect of the floor external inguinal ring is preferred. The surgeon covers his/her palpating index finger with a flexible silicone material surgical finger sheath that has a preperitoneal distention balloon attached thereto and then inserts the covered finger into the prevesical space thereby guiding the preperitoneal distention balloon adjacent to the catheterized bladder. The preperitoneal distention balloon is commercially available from Origin Medsystems, located in Menlo Park, Calif.

Before inserting the finger sheath into the patient's body, the distention balloon's inflation volume is confirmed and the number of insufflation pumps required to achieve an approximate spherical volume of 200 cc is noted. The preperitoneal distention balloon is non-traumatically inserted into the potential space, inflated to 200 ml and left in place for approximately 2 minutes. During this time, the surgeon gently tugs on the balloon to insure that the balloon is adequately distended for fixation within the cavity. As the preperitoneal distention balloon is deflated and the device is removed, digital confirmation of the adequacy of this space is performed. The cavity is irrigated with antibiotic solution, and the prosthetic reservoir is inserted and inflated with 100 cc normal saline. Closure of the small fascial defect is not required.

The device proposed herein would allow such distension to take place as a possible improved alternative to the rigid trocar balloon.

What is claimed is:

1. A device for radially distending a soft tissue space comprising:

(a) a glove, said glove having at least one finger compartment for covering at least one finger of a hand, said finger compartment having a proximal and a distal end; and (b) a distention balloon attached to the distal end of at least one finger compartment, said balloon having a relative deflatable position in relation to said glove and a relative inflatable position in relation to said glove, wherein when said balloon is in the inflatable position the soft tissue space dilates to a desired position.

2. The device of claim 1 wherein said glove is made of a silicone material.

3. The device of claim 1 wherein said distention balloon can be inflated to a volume between 50 ml to about 1500 ml.

4. The device of claim 1 wherein said distention balloon has a generally spherical shape.

5. The device of claim 1 wherein said distention balloon has a generally pancake shape.

6. The device of claim 1 wherein said distention balloon has a generally longitudinal shape.

7. The device of claim 1 wherein said distention balloon has a generally oblong shape.

8. The device of claim 1 wherein said distention balloon has a generally ovoid shape.

9. A device for radially distending a soft tissue space comprising:

(a) a glove, said glove having at least one finger compartment for covering at least one finger of a hand, said finger compartment having a proximal and distal end;

(b) a distention balloon attached to the distal end of at least one finger of said glove, said balloon having a relative deflatable position in relation to said glove and a relative inflatable position in relation to said glove;

(c) a fluid flow assembly for inflating and deflating said balloon.

10. The device of claim 9 wherein said glove is made of a silicone material.

11. The device of claim 9 wherein said distention balloon can be inflated to a volume between 50 ml to about 1500 ml.

12. The device of claim 9 wherein said distention balloon has a generally spherical shape.

13. The device of claim 9 wherein said distention balloon has a generally pancake shape.

14. The device of claim 9 wherein said distention balloon has a generally longitudinal shape.

15. The device of claim 9 wherein said distention balloon has a generally oblong shape.

16. The device of claim 9 wherein said distention balloon has a generally ovoid shape.

17. A device for the radially distending a soft tissue space comprising:

(a) a finger sheath for covering at least one finger of a hand, said sheath having a proximal and distal end; and (b) a distention balloon attached to the distal end of at least one finger, said balloon having a relative inflatable position in relation to said finger sheath and a relative deflatable position in relation to said finger sheath wherein when said balloon is in the inflatable position the soft tissue space dilates to a desired position.

18. The device of claim 17 wherein said distention balloon has a generally spherical shape.

19. The device of claim 17 wherein said distention balloon has a generally pancake shape.

20. The device of claim 17 wherein said distention balloon has a generally longitudinal shape.

21. The device of claim 17 wherein said distention balloon has a generally oblong shape.

22. The device of claim 17 wherein said distention balloon has a generally ovoid shape.

23. A device for radially distending a soft tissue space comprising:

(a) a finger sheath for covering at least one finger, said sheath having a proximal and distal end;

(b) a distention balloon attached to the distal end of said sheath, said balloon having a relative deflatable position in relation to said finger sheath and a relative inflatable position in relation to said sheath; and (c) a fluid flow assembly for inflating and deflating said balloon.

24. The device of claim 23, wherein said finger sheath is made of a silicone material.

25. The device of claim 23 wherein said distention balloon can be inflated to a volume between about 50 ml to about 1500 ml.

26. The device of claim 23 wherein said distention balloon has a generally spherical shape.

27. The device of claim 23 wherein said distention balloon has a generally pancake shape.

28. The device of claim 23 wherein said distention balloon has a generally longitudinal shape.

29. The device of claim 23 wherein said distention balloon has a generally oblong shape.

30. The device of claim 23 wherein said distention balloon has a generally ovoid shape.

31. A device for radially distending a soft tissue space comprising:

(a) a mitten for covering a hand, said mitten having a compartment for receiving fingers of a hand, and said mitten having a proximal and distal end;

(b) a distention balloon attached to said distal end of said mitten, said balloon having a relative inflatable position in relation to said mitten and a relative deflatable position in relation to said mitten, wherein when said balloon is in the inflatable position the soft tissue space dilates to a desired position.

32. The device of claim 31, wherein said mitten is made of a silicone material.

33. The device of claim 31 wherein said distention balloon can be inflated to a volume between about 50 ml to about 1500 ml.

34. The device of claim 31 wherein said distention balloon has a generally spherical shape.

35. The device of claim 31 wherein said distention balloon has a generally pancake shape.

36. The device of claim 31 wherein said distention balloon has a generally longitudinal shape.

37. The device of claim 31 wherein said distention balloon has a generally oblong shape.

38. The device of claim 31 wherein said distention balloon has a generally ovoid shape.

39. A device for radially distending a soft tissue space comprising:

(a) a mitten for covering a hand, said mitten having a compartment for receiving fingers of a hand, said mitten having a proximal end and a distal end;

(b) a distention balloon attached to said distal end said balloon having a relative inflatable position in relation to said mitten and a relative deflatable position in relation to said mitten; and (c) a fluid flow assembly for inflating and deflating said balloon.

40. A device of claim 39, wherein said sheath is made of a silicone material.

41. The device of claim 39 wherein said distention balloon can be inflated to a volume between 50 ml to about 1500 ml.

42. The device of claim 39 wherein said distention balloon has a generally spherical shape.

43. The device of claim 39 wherein said distention balloon has a generally pancake shape.

44. The device of claim 39 wherein said distention balloon has a generally longitudinal shape.

45. The device of claim 39 wherein said distention balloon has a generally oblong shape.

46. The device of claim 39 wherein said distention balloon has a generally ovoid shape.

47. A method of manipulating a patients internal bodily area comprising the steps:

(a) creating an incision through a patient's skin to permit entry into the body interior to perform a medical procedure;

(b) inserting at least one palparing finger, that is covered with a surgical protective material and has an inflatable and deflatable distention balloon connected thereto, into an interior bodily area that will be dilated; and (c) inflating the balloon to the desired volume such that the interior bodily area will dilate wide enough so that an ensuing medical procedure can be undertaken.

* * * * *

UNITED STATES PATENT AND TRADEMARK OFFICE
CERTIFICATE OF CORRECTION

PATENT NO. : 5,582,620
DATED : December 10, 1996
INVENTOR(S) : Hirsch

It is certified that error appears in the above-identified patent and that said Letters Patent is hereby corrected as shown below:

In the Abstract, line 6, please delete "An inflation source" and insert --A means-- and line 9, please delete "A valve member" and insert --A means--.

Column 3, line 28, please delete "in".

Column 4, line 16, please delete "a" and insert --an--.

Column 4, line 37, please delete "palparing" and insert --palpating--.

Column 5, line 24, please delete "a" and insert --an--.

Column 5, line 33, please delete "palparing" and insert --palpating--.

Column 5, line 60, please delete "are" and insert --is--.

Column 6, line 30, please delete "are" and insert --is--.

Column 7, line 3, please delete "are" and insert --is--.

Column 7, line 7, please delete "know" and insert --now--.

Column 7, line 11, please delete "palparing" and insert --palpating--.

Column 7, line 22, please delete the first occurrence of the word "the".

UNITED STATES PATENT AND TRADEMARK OFFICE
CERTIFICATE OF CORRECTION

PATENT NO. : 5,582,620
DATED : December 10, 1996
INVENTOR(S) : Hirsch

It is certified that error appears in the above-identified patent and that said Letters Patent is hereby corrected as shown below:

In the claims, column 10, line 35, please delete "palparing" and insert --palpating--.

Signed and Sealed this

Twelfth Day of May, 1998

Attest:

BRUCE LEHMAN

Attesting Officer

Commissioner of Patents and Trademarks